(12) United States Patent
Tiren

(10) Patent No.: US 6,514,192 B2
(45) Date of Patent: Feb. 4, 2003

(54) MEDICAL SYSTEM COMPRISING A MINIATURIZED X-RAY TUBE

(75) Inventor: Jonas Tiren, Uppsala (SE)

(73) Assignee: Radi Medical Technologies AB, Uppsala (SE)

( * ) Notice: Subject to any disclaimer, the term of this patent is extended or adjusted under 35 U.S.C. 154(b) by 73 days.

(21) Appl. No.: 09/783,219

(22) Filed: Feb. 15, 2001

(65) Prior Publication Data

US 2002/0115901 A1 Aug. 22, 2002

(51) Int. Cl.[7] ............... A61N 5/00; A61M 5/00; H01J 35/32
(52) U.S. Cl. ............... 600/3; 604/264; 378/121
(58) Field of Search ............... 378/121, 122, 378/119, 202; 600/3, 463; 604/509, 264, 20; 607/27

(56) References Cited

U.S. PATENT DOCUMENTS

| | | | | |
|---|---|---|---|---|
| 5,303,283 A | * | 4/1994 | Jedlitschka et al. | 378/202 |
| 5,854,822 A | | 12/1998 | Chornenky et al. | 378/122 |
| 5,984,853 A | | 11/1999 | Smith | 600/1 |
| 6,095,966 A | | 8/2000 | Chornenky et al. | 600/3 |
| 6,148,061 A | | 11/2000 | Shefer et al. | 378/121 |
| 6,320,935 B1 | * | 11/2001 | Shinar et al. | 378/119 |
| 6,324,257 B1 | * | 11/2001 | Halavee | 378/121 |
| 6,377,846 B1 | * | 4/2002 | Chornenky et al. | 604/20 |

FOREIGN PATENT DOCUMENTS

| | | |
|---|---|---|
| DE | 198 42 466 | 4/2000 |
| WO | 97/07740 | 3/1997 |
| WO | 99/44687 | 9/1999 |

* cited by examiner

Primary Examiner—Eric F. Winakur
Assistant Examiner—Nikita R Veniaminov
(74) Attorney, Agent, or Firm—Foley & Lardner

(57) ABSTRACT

Medical system comprising an X-ray tube unit catheter 302 and an X-ray tube unit including a miniaturised X-ray tube 301, wherein the X-ray tube unit is adapted to be inserted into the X-ray tube unit catheter in order to generate X-ray radiation at a treatment position in a vessel within a human or animal body. The X-ray tube is provided with a distal electrical pole and a proximal electrical pole. The proximal pole is connected via an insulated electrical conductor 305 to an external power source. The distal pole is connectable to a conducting means 304 at the inner surface of the catheter wall via distal connecting means 303. The conducting means has a predetermined length extending in the longitudinal direction of the catheter and is connected via an insulated electrical conductor to the external power source. During treatment the X-ray tube unit is adapted to be moved in relation to the X-ray tube unit catheter, wherein the distal pole is electrically connected to the conducting means.

26 Claims, 5 Drawing Sheets

MEDICAL SYSTEM COMPRISING A MINIATURIZED X-RAY TUBE

FIELD OF THE INVENTION

The present invention relates to a medical system, a method of using the system, and a hollow X-ray tube unit catheter according to the preambles of the independent claims.

In general the present invention relates to connecting a miniature X-ray tube for in vivo use to an electrical power source. A miniature X-ray tube according to the invention is, for example, useful in applications for prevention of restenosis and for treating diseases, such as cancer, in a living body.

BACKGROUND OF THE INVENTION

In treating stenosis in coronary arteries, a restenosis occurs in 30–60% of the cases. It is known that a treatment with beta- or gamma- (X-ray) radiation will decrease the occurrence of restenosis substantially.

Another example of an application of the present invention is treatment of cancer tumors where it is desired to deliver radiation locally.

Methods to apply the radiation to the site of treatment are presently subject to intensive research. Generally, a hollow catheter is inserted into the body, typically via an artery, in such a way that its distal end is placed near the site of treatment. A source of radiation attached to the distal end of an elongated member is inserted into the hollow catheter, and is forwarded until the radiation source is disposed at a proper position for radiating the site of treatment. In the specific case of treating cardiac vessels, the catheter is placed near the cardiac vessel tree (this catheter often called a "guide catheter"). A very thin wire—called guide wire—is then used to probe further and reach the site where treatment shall be performed. The therapeutic device is moved along this wire, i.e. by threading the device onto the guide wire. It is obvious that the therapeutic device has to have a hole close to its distal end in order to do this. Radiation treatment methods using radioactive pellets, wires or balloons etc. as radiation source is known in the art. Since these methods have some drawbacks, such as the need for substantial efforts to control radiation in the environment outside the patient, the use of a nature electrical X-ray tube including a cold cathode has been proposed. Such a tube may be switched on and off due to its electrical activation. An example of such an X-ray tube is described in the U.S. Pat. No. 5,854,822 as well as in U.S. Pat. No. 5,984,853.

A conventional miniature electrical X-ray tube requires electrical conductors to connect the tube, i.e. its anode and cathode, to an external power supply. Conventionally, two conductors, one for the cathode and one for the anode of the tube are connected to the tube, preferably, and as known from prior art in a coaxial arrangement. FIG. 1 schematically illustrates an X-ray tube according to this prior art. However, due to the small dimensions used, the outer diameter of the connecting cable is typically in the range of 1–5 mm when used for cancer treatment and less than 2.0 mm when used in cardiology, and the high voltages used, typically 20 kV, the probability for electrical breakdown between the connections to the tube is considerable. The European Patent application No. 00850173.6, filed Oct. 24, 2000, by the same applicant as the present application, relates to a medical device that is directed to solve that problem. Principally and in short the problem is solved by connecting the proximal pole of the X-ray tube to the external power source via an electrical conductor integrated in the elongated X-ray tube unit that is inserted into an X-ray tube unit catheter. The distal pole of the X-ray tube is connected to an electrical connection arranged at the inner surface of the vertical distal end of the catheter. The electrical connection is then connected to the external power source via an electrical conductor integrated into the wall of the catheter.

It has not been widely recognized to date the importance to center the X-ray source in the cardiac vessel during the radiation treatment. The electrical X-ray source emits a spectrum of radiation in the range of 8–20 kV (for a 20 kV driven device). The lower energies will not penetrate as far into the tissue as the higher energies. Also, even the higher energies have a clear dose fall-off in the tissue of interest. It has recently been found that an optimal target dose of about 16 Gy should be delivered 0.7 mmn into the vessel wall for to achieve the best clinical results. The comparatively rapid dose fall off is also an advantage, because the amount of radiation delivered to healthy tissue further away from the source of ionizing radiation is reduced, as compared to for instance Gamma emitting sources such as Ir-192.

Not centering the soft X-ray emitter may result in too low radiation dose delivered to the part of the vessel wall that is farthest away from the source and too high doses delivered to the tissue that is closest to the wall. FIG. 5 shows the calculated radiation profile in the walls of a 3 mm vessel where the source of ionizing is placed in direct contact to the wall and in the center respectively. As can be seen the farthest wall receives too low doses, and the wall in contact receives too high doses.

In addition to the above, an electrically activated X-ray device can essentially be regarded as a point source. Since the treated site is usually longer than the approximately 1 mm length such a device will cover, the device must be pulled back during the treatment.

U.S. Pat. No. 6,148,061 is primarily directed to a miniature X-ray unit provided with an X-ray transmission window through which X-rays exits the unit. It is also briefly discussed that if the radiation dose must be delivered to a portion of an artery longer than the length of the X-ray window, the unit must be moved while in the activated state along the artery lumen. This can be accomplished by feeding the X-ray unit into, or out of, the guide catheter at the insertion location. The X-ray unit is preferably moved along the length of the treatment region under computer control to insure the correct X-ray dose is delivered to each location along the artery. After treatment, the unit is turned off and removed from the guide catheter.

The benefit of centering the catheter in a vessel is shortly commented in U.S. Pat. No. 6,148,061 where the X-ray unit is centered in an artery to achieve uniform dose delivery around the inner wall of the artery. The X-ray unit can be centered by providing a centering balloon or other inflatable device around the X-ray unit.

U.S. Pat. No. 6,095,966 describes an X-ray device for delivering localized radiation to an interior of a body. The device includes an inflatable balloon arranged around the X-ray emitter to provide a cooling solution to cool the X-ray emitter and dissipate the potentially damaging heat. This known device is positioned at the treatment position by means of the inflated balloon. The device is particularly suited to esophageal applications where it is not so crucial to temporarily block the lumen as in blood vessels.

One object of the present invention is to achieve a medical system adapted to perform treatment at treatment sites having a length of several mm and at the same time achieving a high security with regard to avoiding electrical breakdown between the connections to the tube.

One further object of the present invention is to achieve a medical system where the generated X-ray radiation is conformably applied at a treatment position in a blood vessel and where blood may pass the X-ray tube catheter during the treatment.

SUMMARY OF THE INTENTION

The above-mentioned objects are obtained by a medical system, an elongated X-ray tube unit catheter and also by a method of using the medical system according to the characterizing portions of the independent claims.

Preferred embodiments are set forth in the dependent claims.

According to one preferred embodiment of the present invention one of the conductors for supplying voltage to the X-ray tube is integrated with, or attached to, the hollow catheter used to provide a path for inserting the X-ray source. At the distal end of the hollow catheter, said conductor is exposed at the inside of the hollow catheter to exhibit a terminal surface. The electrical connection to the X-ray tube is at one end (the proximal end when inserted into the hollow catheter) connected to a single electric cable, while the other end (the distal end when inserted into the hollow catheter) is provided with a terminal end surface adapted to achieve an electrical connection to the inner surface along a predetermined length of the hollow catheter when inserted into said catheter.

Another great advantage is that the X-ray tube unit with the radiation source need not be sterilized because it is inserted into the hollow catheter that has an open proximal end to receive the tube unit and a closed distal end. Therefore only the catheter needs to be sterilized in that the X-ray tube unit is never in contact with body tissue. Thus, the X-ray tube unit itself may be reused without sterilization. This should be compared with prior art systems where the insertion catheter (or guide catheter) has an open distal end and where the radiation source unit is in contact with body tissue.

A thirs great advantage of the present invention is that, if, due to unforeseeable circumstances any part of or the whole X-ray tube is damaged in any way, no parts would be spread inside the body but would instead be kept inside the hollow catheter.

The catheter further is improved in order to center the catheter in a vessel while still allowing blood flow—at least partly—to pass the device. This is an important aspect in order to supply blood to the parts of the tissue that obtain their blood supply distally from the device.

A fourth advantage of the present invention according a preferred embodiment is that the dosimetry, i.e. the control of the dose delivered to the tissue is greatly enhanced.

A fifth great advantage is that the catheter will help heat transfer, since the electrically conducting layer described in more detail below, also will aid the heat flux from the tube to be distributed away from the source. The plastic further helps as a thermal isolator.

DETAILED DESCRIPTION OF EMBODIMENTS

Figure 1:
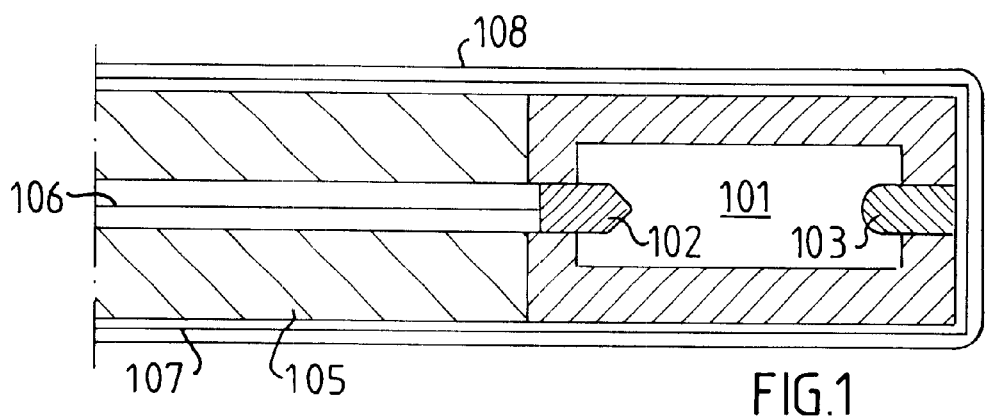
FIG. 1 is a cross-sectional view of a miniature X-ray tube illustrating the prior art.

Miniature cold cathode X-ray tubes are described in for instance U.S. Pat. No. 5,854,822. The principle for such a device according to the prior art is illustrated in FIG. 1. Briefly, such a device is essentially a vacuum diode, with a vacuum cavity 101 in which there is an anode 102 and a cathode 103. Designed for Fowler-Nordheim emission of electrons, once emission has occurred, the electrons are accelerated towards the anode, where they will produce radiation on impact. The radiation characteristics are determined by inter alia the elements used in the anode and the materials used in the vacuum enclosure as well as the accelerating (applied) voltage.

The X-ray tube is connected by a coaxial cable 105 with core and shield leads 106 and 107, respectively, to an external power unit (not shown). The device is further insulated and protected by an insulation layer 108.

Figure 2:
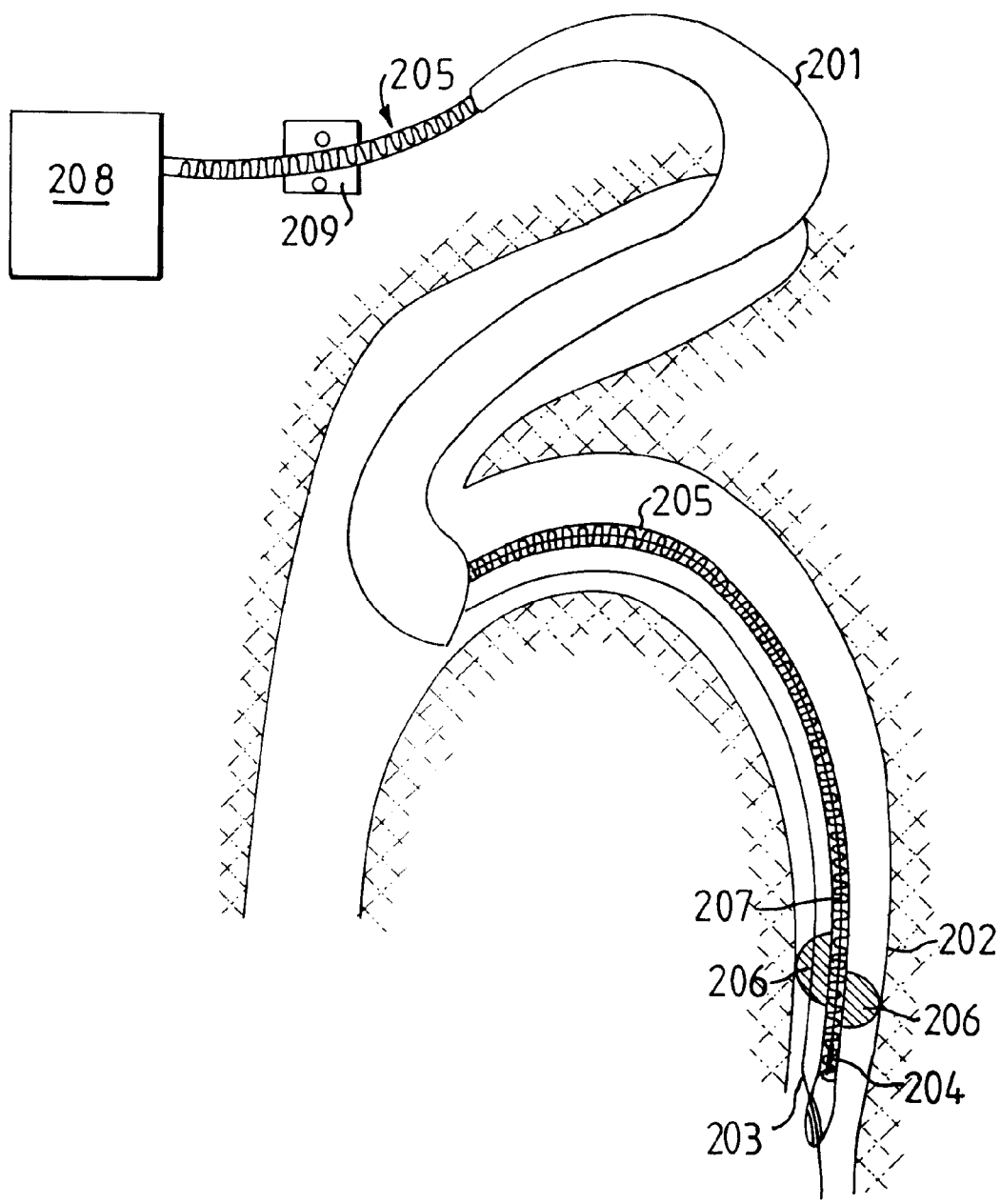
FIG. 2 shows an overview of the medical system according to the present invention.

FIG. 2 shows an overview of the system according to the present invention. First, a guide catheter 201 is inserted into e.g. the femoral artery and moved into position close to the cardiac vessel 202 to be treated. A guide wire 203 is used to probe further to the site where the treatment (balloon dilatation) is performed. Many different types of guiding extensions (e.g. provided with a hole where the guide wire runs) are described in the prior art that may be applied on a catheter according to the present invention. The present invention may be used with any type of guiding extension or even without an extension.

The cold cathode miniature X-ray tube unit 204 is inserted into the X-ray tube unit catheter 205, which has then been moved into position. It is also possible to have the x-ray tube unit 204 inserted beforehand. Shown are examples of a positioning means 206 that performs a centering function, here in the form here of small inflatable balloons. One of the electric poles of the X-ray tube is connected by an insulated electrically conducting wire 207 to the external power source 208. The second electrode of the X-ray tube is connected to the inside of the centering catheter wall which has an electrically conducting surface that may extend over parts or over the entire inner surface of the X-ray tube catheter. This feature will be described in detail below. In addition a mechanical (manual or computer controlled) moving device 209 can be used in order to move, relative the catheter, the X-ray tube e.g. in a proximal direction in a controlled manner.

Figure 3A:
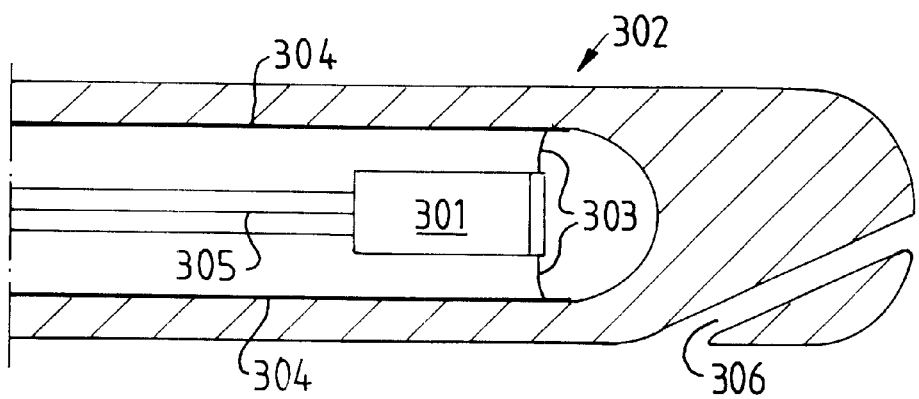
FIGS. 3a and 3b show embodiments of the distal electrical connection between the inner surface of the catheter and the miniature X-ray tube in more detail.
Figure 3B:
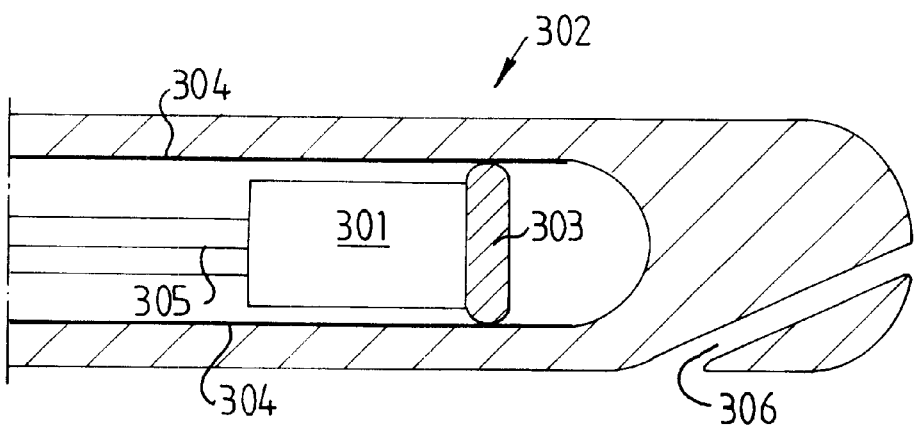

The distal electrical connection between the X-ray tube unit and the X-ray tube unit catheter is shown in more detail in FIGS. 3a and 3b. The series resistance caused by the contacts and the electrically conducting Mm (see below 304)

is not critical. A typical X-ray tube operates at 20,000 V and at 1–10 microamperes. A series resistance of 10 Mohms would result in an (unwanted) voltage drop of 200 V, 1% of the applied voltage. This may be totally neglected. An even higher series resistance such as 100 Mohms may be tolerated, although it should be taken into account when for instance calculation radiation characteristics.

What is important however, is that any series resistance to the human body should be orders of magnitude larger than the series resistance in the electrical connection. But in order to exemplify, using a cylindrical geometry of a 0.1 micrometer gold film of 1.5 meters length would result in an theoretical series resistance of some 50 Ohms.

The X-ray tube 301 may have a cylindrical outer shape. However, other shapes are naturally possible without departing from the scope of the invention as defined in the appended claims.

In FIGS. 3a and 3b, respectively, the X-ray tube 301 is inserted into the X-ray tube unit catheter 302. The distal end of the electrical X-ray tube 301 is supplied with a distal connecting means 303 that will create a secure electrical contact with the conducting means 304 at the interior surface of the catheter.

According to a preferred embodiment the distal connecting means 303 is in the form of one or many spring-like connectors 303. This embodiment is illustrated in FIG. 3a.

FIG. 3b illustrates another preferred embodiment of the distal connecting means 303 where the connecting means instead is an extension that extends in a radial direction outside the outer surface of the catheter. The dimension of the extension is related to the inner diameter of the catheter such that it secures electrical connection between the distal pole of the X-ray tube and the conducting means 304.

The diameter of the extension is preferably slightly smaller than the inner diameter of the catheter. Electrical connection will be secured as long as any part of the extension is in physical contact with the inner surface.

The extension is made from any electrically conductive material and may have a solid band like or net-like structure.

To the proximal end of the X-ray tube, a single lead insulated electrical wire 305 is connected. Also shown is a hole 306 to be used for a guide wire.

The interior surface of the catheter may for example be made of a film of polyetylene-teftalat. Onto this film a very thin layer of metal (or other conducting material) has been deposited onto its surface. It is important to carefully choose the conducting layer material and its thickness to avoid excessive radiation absorption in the layer, because this would stop the radiation from reaching the target tissue. If heavy materials such as gold are chosen, thin layers must be used. If on the other hand, light materials such as Aluminum are chosen, thicker layers may be allowed. The film is then wrapped to produce a circular insertion. This kind of films is comparatively stiff, so the film will stay in place after it has been inserted into the catheter. The film position may further be secured by bonding the film to the catheter wall at its distal end, for example.

It can also be a film of graphite or a metal deposited directly onto the interior surface of the catheter.

It is advantageous to use a coating of the wall that is close to a coaxial symmetry because of electrical dielectric strength considerations.

The catheter may have the inner surface conducting all the way from its distal to its proximal end, or a lumen in the catheter can be provided with an electrical wire that is connected to the surface, not extending all the way to the proximal end. These two embodiments are illustrated in FIGS. 4a and 4b, respectively.

Figure 4A:
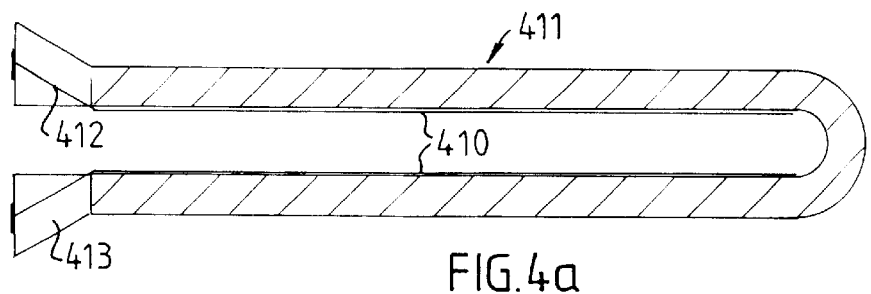
FIGS. 4a and 4b exemplify the conducting paths through the catheter as well as the proximal contact arrangement.

In FIG. 4a a conductive inner surface 410 extends all the way to the proximal end of the X-ray tube unit catheter 411. At the proximal end is arranged a contact arrangement such as a metal cone 412 with an insulation 413, the cone being pushed into the catheter and joined to the catheter by standard methods such as welding, gluing etc. This contact is in its turn connected by e.g. a cable to the power supply.

Figure 4B:
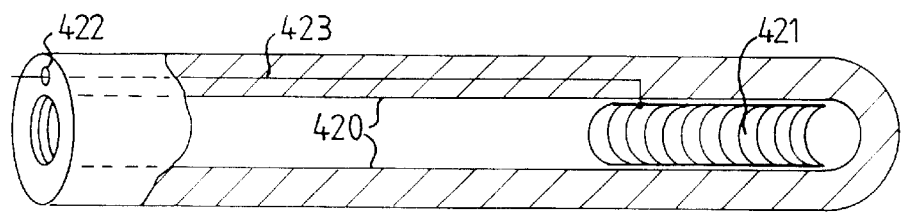

In FIG. 4b, the inner surface 420 of the catheter is only conductive in its distal portion, i.e. the conducting area 421 is only extending partially through the catheter. The length of this distal portion must be longer than the length of the treated vessel segment. Such a segment is typically only 10 mm or less but may be as long as 30–50 mm. The length of the conducting portion is typically less than 50–100 mm but could be longer. A lumen 422 in the catheter wall provides a channel for an electrical conductor 423 to be attached at the conducting area.

The electrical conductor 423 may be a thin gold or copper wire, typically, although any other metal could be used. Tungsten would be another choice since this material is quite strong. It is attached to the conducting portion by e.g. soldering. Also a ring shaped contact (not shown) could be used in the distal end of the wire, having the additional benefit of being X-ray opaque, giving an additional way to accurately positioning the catheter into the vessel.

The centering function is important in order to achieve control of the dosimetry, i.e. the delivered dose to the target tissue in the vessel wall. It has been reported that an optimal dose is 16 Gy that should be delivered to 0.7 mm depth inside the vessel tissue. It is important not to under dose the tissue, because this has been reported to enhance the re-growth of tissue instead of inhibiting this. It is also desirable to keep the maximum dose (given to the surface) as close as possible to the 16 Gy prescribed at 0.7 mm depth. Because of the exponential decay with distance, which is inherent to radiation, it is not physically possible to achieve exactly the same dose. For low energy sources such as miniature X-ray devices this a problem; these have radiation fall off that is comparable to state of the art beta emitting sources, such as the Y/Sr source by Novoste Inc. It is considered that it is important to keep the dose at the tissue surface below 50 Gy.

Figure 5:
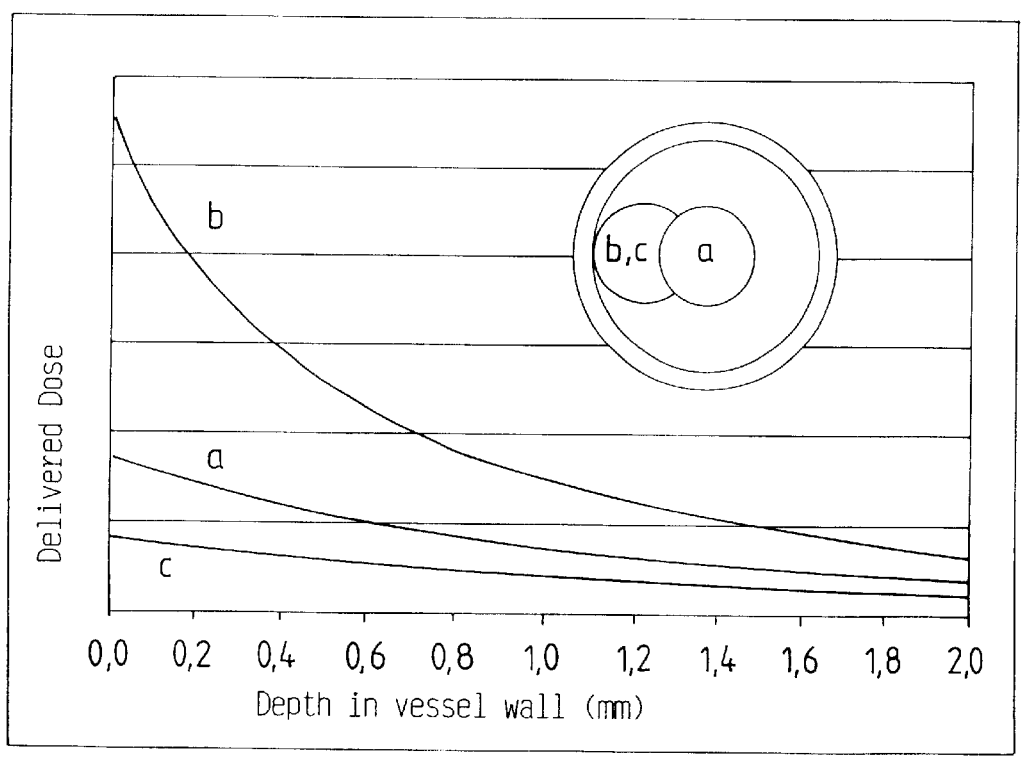
FIG. 5 shows radiation dose fall off in tissue for a centered and non-centered miniature X-ray source, respectively, in a 3 mm vessel.

In FIG. 5, the resulting dose deliver profiles are shown for a miniature electrical cold cathode X-ray tube as calculated from radiation attenuation data given by the National Institute of Standards and Technology (NIST) for various parts, polymers and tissue. The calculation is done for a centered device inserted into a 3-mm diameter vessel. The curve "a" shows the dose fall off for a perfectly centered device. The curves "b" and "c" shows the dose fall off for a maximally off-centered device, i.e. touching the vessel wall. The curve "b" is the dose delivered to the tissue in contact with the miniature X-ray device, and the curve "c" is the dose delivered to the tissue in the opposite wall.

For the off-centered case, the dose delivered to the vessel wall in contact with the miniature device is almost 6 times higher and the dose delivered at 0.7 mm tissue depth is almost half of the prescribed dose. This would correspond to almost 100 Gy to the tissue wall (as compared to about 30 Gy in the centered case and an under dose of about 7.5 Gy.

The requirement of the centering can be estimated using the same type of calculation. The result is that, for a 3-mm vessel as an example, the centering must be accurate to +/−0.5 mm or better within the vessel. This will result in a surface overdose of <50 Gy as well as an acceptable target tissue under dose of >12 Gy, which must be considered adequate as several investigations have used this dose, and although not finding an optimal result, a significant improvement has been obtained.

Figure 6A:
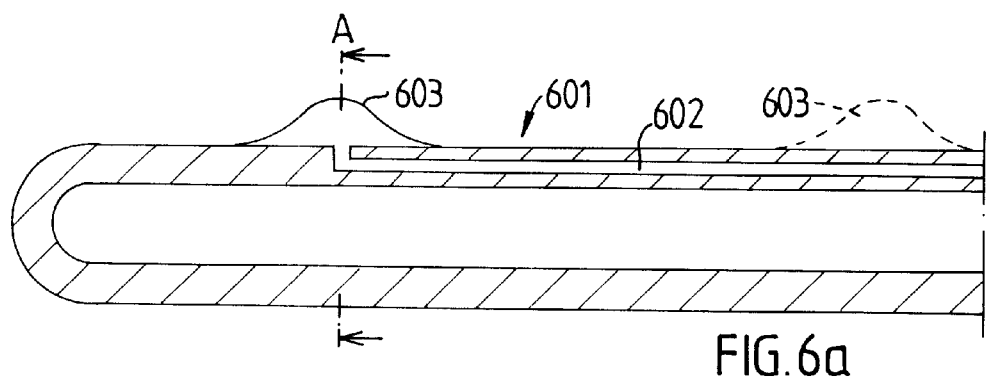
FIGS. 6a and 6b show a preferred embodiment of a centering function.
Figure 6B:
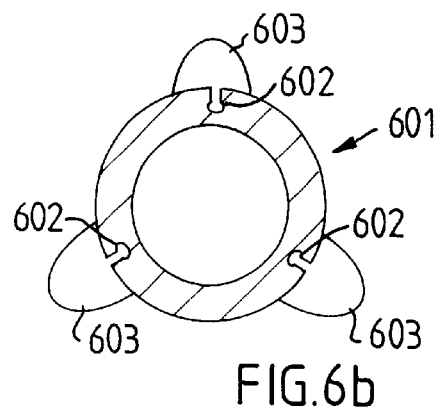

The centering function may be achieved in many ways, most readily by using inflatable balloons. FIG. 6 shows a first embodiment of the centering function. In FIG. 6, the electrical connections described above are excluded, again for reasons of clarity.

The X-ray tube unit catheter 601 is provided with a lumen at 602 and one or more groups of three inflatable balloons 603 disposed on the catheter surface, arranged preferably with a 120-degree angular division. It would also be possible to use two inflatable balloons arranged with a 180-degree angular division or four inflatable balloons arranged with a 90-degree angular division. Even a higher number of balloons are possible to use.

The balloons are inflated by e.g. saline solution supplied through the lumen. Contrast medium must not be used because the centering balloons must be radiation transparent. Preferably, more than one group of balloons is used as shown in FIG. 6 in order to correctly align the X-ray source within the above mentioned tolerance.

The arrangement of the balloons is such that blood may pass between the balloons in their inflated state.

It is desirable to be able to check that the balloons have been deflated after the treatment. Since the balloons, during therapy is radiation transparent, this checking may easily be achieved by replacing the saline solution with a contrast solution after the treatment, and then deflating the balloons prior removal of the centering catheter.

Preferably the centering balloons are spaced by 1–50 mm in the longitudinal direction, and that the balloons are less than 2 mm wide and 10 mm long.

Figure 7A:
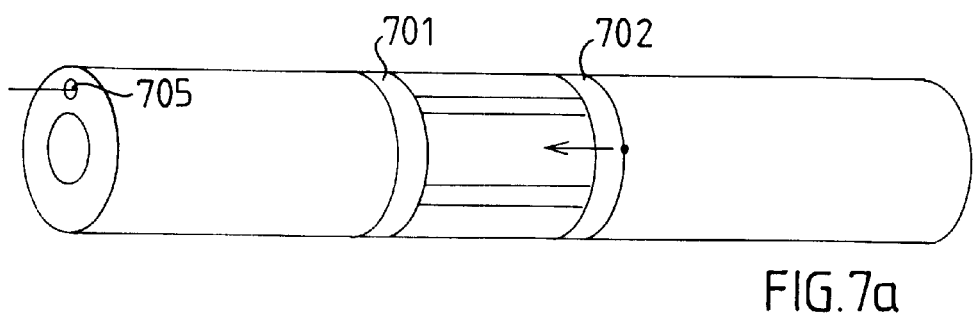
FIGS. 7a and 7b show an alternative embodiment of a centering function.
Figure 7B:
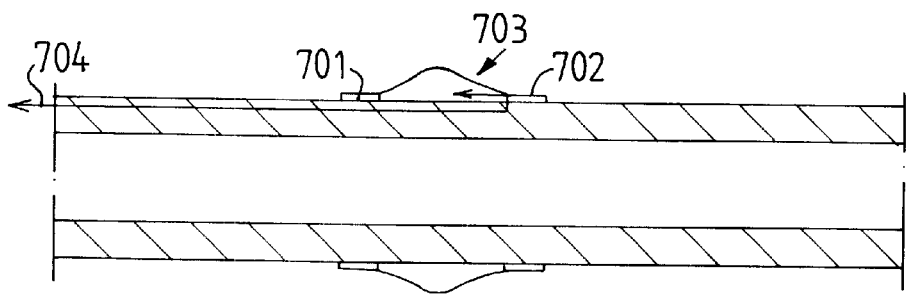

According to an alternative embodiment of the present invention the centering function is achieved by a more mechanical approach such as disclosed in FIG. 7. In the embodiment shown in FIG. 7, two rings 701 and 702 are joined by three or more band-like structures 703 of a material that is reasonably radiation transparent, such as Teflon or Mylar. Mylar has an X-ray attenuation for the energies of interest that is very close to blood. The most distal ring 702 is attached to a wire 704, provided through a lumen 705 in the centering catheter. When the wire is pulled the rings move toward each other and the band-like structure expands and performs a centering function. It is important that the band-like structure 703 automatically returns to the initial state, i.e. the non-centering state, when the pulling force of the wire 704 ceases. The return to the initial state happens automatically when the treatment has been performed or e.g. the wire is damaged or broken.

Figure 8A:
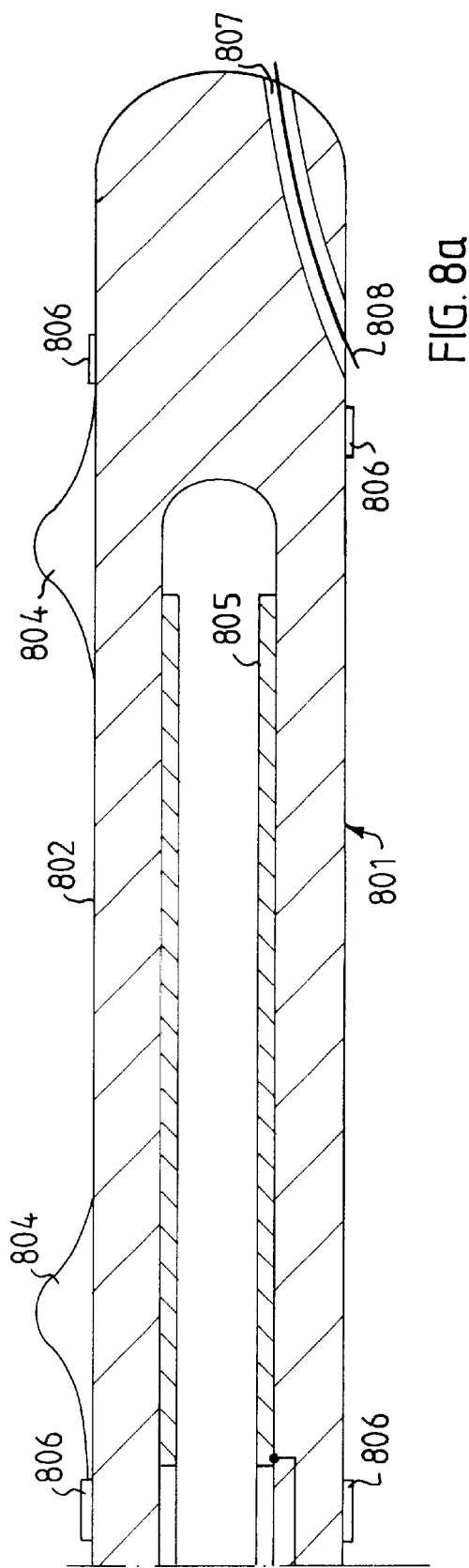
FIGS. 8a and 8b show the distal part of the catheter with the centering function according to the preferred embodiment.
Figure 8B:
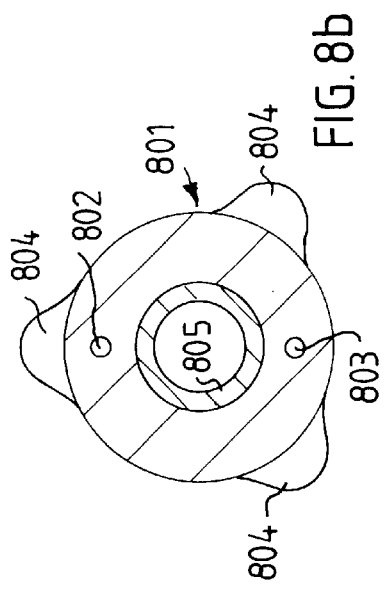

One embodiment of the complete catheter is shown in FIG. 8. The hollow catheter is typically made of a plastic material. Examples of plastics that are usable, alone or in combinations, are Teflon, Polyamides, polyethylene, silicone, PVC etc. These are common materials used for catheters. In some of the embodiments it is important to ensure a high electrical breakdown for regulatory safety reasons, and die choice of material will be narrowed down to some extent. The catheter 801, having a typical outer diameter of less than 2 mm and a typical inner diameter of 1.5 mm is provided with lumens 802 and 803, respectively. (It should be noted that, in all descriptions disclosed herein, a catheter is assumed to have a center lumen by definition, in which the miniature X-ray source is inserted.) The lumen 802 (which may be more than one) supplies the balloons 804 with an inflation solution, e.g. saline. The methods to do so and manufacturing such balloons on a catheter are well known.

The lumen 803 provides the electrical connection to the conduction layer 805 inside the catheter. Radio opaque markers 806 are arranged preferably distally and proximally said positioning means, for simplifying correct positioning inside the vessel as well as a hole 807 for a guide wire 808.

Heat is a general issue for this application. The temperature increase to the surrounding tissue should not exceed some 3 degrees C. (41 degrees C. in absolute terms). A typical applied voltage is 20,000 V and the current is typically microamperes. The power delivered to the very small volume of the anode is then some 0.2 W. This power is essentially totally converted to heat in the anode (only a very small fraction is converted into radiation). This heat must be transported away. Analysis show that the catheter helps bringing the temperature increase down to approximately less than 1 degrees C., as compared to prior art devices that will have a temperature increase of some 3 degrees C. This in turn could be used either to keep the temperature increase low, or to increase the power of the device, without passing the critical point of 41 degrees C. The following benefit is more radiation energy per time unit and therefore shorter treatment times. The latter is important because the time in the catheterisation laboratory is very expensive. Also patient discomfort is reduced.

The methods for manufacturing such catheters are known to the skilled person in the art. Typically a multi lumen catheter is extruded without its distal closed end. The distal, electrically conducting film is added, e.g. by inserting a foil with a conducting surface, as mentioned above, either all the way to the proximal end, or to the lumen, with its wire, in this embodiment. The electrical connection is secured to the wire alternatively to the distal end. The balloons are attached to the lumen(s) intended to be connected to the same. The catheter is sealed with a part also provided with the hole for the guide wire. A proximal electrical connection as well as a proximal connection for the inflation is made. Radio opaque markers are added.

There is also a possibility to arrange the conducting means at the inner surface of a catheter that is not provided with the positioning means (e.g. the balloons) that centres the catheter. Then it is possible to treat a larger area by pulling the X-ray tube unit passed the treatment position.

The present invention is not limited to the above-described preferred embodiments. Various alternatives, modifications and equivalents may be used. Therefore, the above embodiments should not be taken as limiting the scope of the invention, which is defined by the appending claims.

What is claimed is:

1. A medical system comprising:
    an X-ray tube unit catheter defining a catheter wall; and
    an X-ray tube unit including a miniaturised X-ray tube, wherein the X-ray tube unit is adapted to be inserted into the X-ray tube unit catheter to generate X-ray radiation at a treatment position in a vessel within a human or animal body, wherein said X-ray tube is provided with a distal electrical pole and a proximal electrical pole, wherein the proximal pole is connected via an insulated electrical conductor to an external power source, wherein the distal pole is electrically connected to a conducting means at an inner surface of the catheter wall via distal connecting means, wherein said conducting means has a predetermined length extending in a longitudinal direction of the catheter and is connected via an insulated electrical conductor to the external power source, and wherein during treatment, the X-ray tube unit is adapted to be moved in relation to the X-ray tube unit catheter.

2. The medical system according to claim 1, wherein said conducting means is arranged in the distal end of the catheter.

3. The medical system according to claim 1, wherein said conducting means covers the entire inner surface of the catheter along the predetermined length of the catheter.

4. The medical system according to claim 1, wherein said conducting means covers parts of the inner surface of the catheter along the predetermined length of the catheter.

5. The medical system according to claim 1, wherein said conducting means covers the entire inner surface of the catheter along essentially the whole catheter.

6. The medical system according to claim 1, further comprising:
X-ray tube unit moving means adapted to move the X-ray tube unit in relation to the catheter.

7. The medical system according to claim 6, wherein said X-ray tube unit moving means is adapted to pull the X-ray tube unit in a proximal direction in relation to the catheter, from a distal position where the X-ray tube is positioned distally said treatment position to a proximal position where the X-ray tube is positioned proximally said treatment position.

8. The medical system according to claim 1, wherein said distal connecting means comprises one or more spring-like connectors that extend in a radial direction.

9. The medical system according to claim 1, wherein said distal connecting means comprises an extension that extends in a radial direction.

10. The medical system according to claim 1, wherein said catheter comprises positioning means close to its distal end arranged to position the distal end of the X-ray tube unit catheter in the vessel at the treatment position, wherein said positioning means is adapted to position the catheter such that blood may pass the positioning means and that a center axis of the catheter essentially coincides with a center axis of the vessel at the treatment position.

11. The medical system according to claim 10, wherein said positioning means comprises one or more balloons arranged at the outer surface of the catheter.

12. The medical system according to claim 11, wherein a first group of balloons is arranged symmetrically in a cross-sectional plane of the catheter.

13. The medical system according to claim 12, wherein a second group of balloons is arranged in a cross-sectional plane axially separate from the first group of balloons.

14. The medical system according to claim 11, wherein the one or more balloons are inflated by a saline solution supplied through a lumen in the catheter wall.

15. The medical system according to claim 10, wherein said positioning means comprises a band-like structure that is extracorporeally activated.

16. The medical system according to claim 15, wherein said positioning means further comprises two rings that are joined together by three or more band-like structures, wherein the most distal of the two rings is attached to a wire provided through a lumen in the catheter, and wherein when the wire is pulled, the distal ring moves toward the other ring and the band-like structure expands and performs a centering function.

17. The medical system according to claim 16, wherein said band-like structure and rings are made out of a material that is reasonably radiation transparent.

18. An X-ray tube unit catheter comprising:
a central lumen into which an X-ray tube unit, including a miniaturized X-ray tube, is adapted to be inserted to generate X-ray radiation at a treatment position in a vessel within a human or animal body,
wherein an inner surface of the central lumen is provided with conducting means having a predetermined length and extending in a longitudinal direction of the catheter, and wherein the conducting means is connected via an insulated electrical conductor to an external power source.

19. The X-ray tube unit catheter according to claim 18, wherein said conducting means is arranged in a distal end of the catheter.

20. The X-ray tube unit catheter according to claim 18, wherein said conducting means covers the entire inner surface of the catheter along the predetermined length of the catheter.

21. The X-ray tube unit catheter according to claim 18, wherein said conducting means covers parts of the inner surface of the catheter along the predetermined length of the catheter.

22. The X-ray tube unit catheter according to claim 18, wherein said conducting means covers the entire inner surface of the catheter along essentially the whole catheter.

23. A method of using a medical system comprising the following steps:
a) inserting an X-ray tube unit catheter into a vessel of a human or animal body to a treatment position;
b) inserting an X-ray tube unit into the catheter;
c) performing treatment by activating the X-ray tube;
d) pulling the X-ray tube in a proximal direction;
e) deactivating the X-ray tube when it has passed the treatment position;
f) removing the X-ray tube unit from the vessel; and
g) removing the X-ray tube unit catheter from the vessel.

24. The method of using a medical system according to claim 23, further comprising the following sub-steps:
a1) inserted between steps a) and b): positioning the catheter by activating a positioning means arranged close to a distal end of the catheter to position the distal end of the catheter in the vessel at the treatment position, such that blood may pass the positioning means and that a center axis of the catheter essentially coincides with a center axis of the vessel at the treatment position; and
f1) inserted between steps f) and g): deactivating the positioning means.

25. A method of using a medical system comprising the following steps:
a) inserting an X-ray tube unit catheter into a vessel of a human or animal body to a treatment position, wherein an X-ray tube unit is positioned within the catheter;
b) performing treatment by activating the X-ray tube;
c) pulling the X-ray tube in a proximal direction;
d) deactivating the X-ray tube when it has passed the treatment position;
e) removing the X-ray tube unit from the vessel; and
f) removing the X-ray tube unit catheter from the vessel.

26. The method of using a medical system according to claim 25, further comprising the following sub-steps:

a1) inserted between steps a) and b): positioning the catheter by activating a positioning means arranged close to a distal end of the catheter to position the distal end of the catheter in the vessel at the treatment position, such that blood may pass the positioning means and that a center axis of the catheter essentially coincides with a center axis of the vessel at the treatment position; and e1) inserted between steps e) and f): deactivating the positioning means.

* * * * *